(12) United States Patent
Iuchi et al.

(10) Patent No.: US 10,350,569 B2
(45) Date of Patent: Jul. 16, 2019

(54) METHOD FOR PRODUCING MICROCAPSULE

(75) Inventors: Seiji Iuchi, Takarazuka (JP); Rie Takabe, Nishinomiya (JP)

(73) Assignee: SUMITOMO CHEMICAL COMPANY, LIMITED, Chuo-ku, Tokyo (JP)

( * ) Notice: Subject to any disclaimer, the term of this patent is extended or adjusted under 35 U.S.C. 154(b) by 0 days.

(21) Appl. No.: 13/320,568

(22) PCT Filed: May 28, 2010

(86) PCT No.: PCT/JP2010/059489
§ 371 (c)(1),
(2), (4) Date: Nov. 15, 2011

(87) PCT Pub. No.: WO2010/137743
PCT Pub. Date: Dec. 2, 2010

(65) Prior Publication Data
US 2012/0065070 A1 Mar. 15, 2012

(30) Foreign Application Priority Data
May 29, 2009 (JP) ................................. 2009-130143

(51) Int. Cl.
*A01N 25/28* (2006.01)
*B01J 13/02* (2006.01)
*B01J 13/16* (2006.01)

(52) U.S. Cl.
CPC .............. *B01J 13/16* (2013.01); *A01N 25/28* (2013.01)

(58) Field of Classification Search
CPC ........ A01N 25/28; A01N 25/04; A01N 51/00; B01J 13/16
USPC ............. 504/359; 424/408; 514/4.5; 264/4.7
See application file for complete search history.

(56) References Cited

U.S. PATENT DOCUMENTS

| 1,937,969 | A * | 12/1933 | Knight ........................... 424/731 |
| 4,140,516 | A | 2/1979 | Scher |
| 4,851,227 | A | 7/1989 | Markus et al. |
| 6,113,936 | A | 9/2000 | Takebayashi et al. |
| 2003/0119675 | A1 * | 6/2003 | Wolf et al. ..................... 504/308 |
| 2009/0060966 | A1 | 3/2009 | Tsuda |
| 2009/0062350 | A1 | 3/2009 | Tsuda |
| 2009/0142406 | A1 * | 6/2009 | Tanedani ....................... 424/497 |

FOREIGN PATENT DOCUMENTS

| CA | 2385991 | A1 | 4/2001 |
| DE | 19947147 | A1 | 4/2001 |
| EP | 0368285 | A2 | 5/1990 |
| EP | 1961303 | A1 | 8/2008 |
| FR | 2392715 | | 12/1978 |
| FR | 2602120 | | 2/1988 |
| JP | 50-116638 | A | 9/1975 |
| JP | 57-24303 | A | 2/1982 |
| JP | 6-256116 | A | 9/1994 |
| JP | 10-7505 | A | 1/1998 |
| JP | 11322587 | A | 11/1999 |
| JP | 2009-062292 | A | 3/2009 |
| KR | 10-2008-0077683 | A | 8/2008 |
| WO | 2003/051116 | A1 * | 6/2003 |
| WO | WO 05/112624 | | * 12/2005 |
| WO | 2007/069461 | A1 * | 6/2007 |

OTHER PUBLICATIONS

International Preliminary Report on Patentability dated Dec. 8, 2011 in International Application No. PCT/JP2010/059489.
Chinese Office Action issued in corresponding Chinese Application No. 201080023634.9 dated Feb. 18, 2013.
Supplementary European Search Report issued in corresponding EP Application No. 10780694.5, dated Nov. 21, 2013.
Japanese Office Action issued in corresponding JP Application No. 2009-130143, dated Sep. 10, 2013.
Taiwanese Office Action issued in corresponding TW Application No. 99116951 dated Jan. 13, 2015, with an English language Translation.
Communication dated Sep. 29, 2015, issued by the European Patent Office in corresponding European Application No. 10 780 694.5.
Communication dated May 25, 2016 from European Patent Office in counterpart Application No. 10 780 694.5.
(Continued)

*Primary Examiner* — Alma Pipic
(74) *Attorney, Agent, or Firm* — Sughrue Mion, PLLC

(57) ABSTRACT

An object of the present invention is to provide a technique for producing a microcapsule containing a pesticidal compound in a fatty acid ester such as methyl O-acetylricinoleate, which delays the release timing of the pesticidal compound as compared to a conventional microcapsule. Provided is a method for producing a microcapsule, which comprises:

(1) keeping a mixture of a pesticidal compound, a compound represented by formula (I):

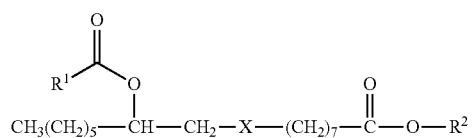

(I)

wherein X represents —$CH_2$—$CH_2$— or —CH=CH—, $R^1$ represents a C1-C4 alkyl group, and $R^2$ represents a C1-C4 alkyl group, and a polyisocyanate at 20 to 60° C. for 3 hours or more;

(2) adding the mixture to water containing a polyol or a polyamine to prepare liquid droplets in the water; and (3) forming a film of polyurethane or polyurea around the droplets.

9 Claims, No Drawings

(56) References Cited

OTHER PUBLICATIONS

Communication dated Jun. 13, 2016 from Korean Intellectual Property Office in counterpart Application No. 10-2011-7028067.
Communication dated Jun. 17, 2016, issued by the Canadian Intellectual Property Office in corresponding Canadian Application No. 2,761,500.
Communication dated Dec. 7, 2016 from the Korean Intellectual Property Office in counterpart application No. 10-2011-7028067.
Indian Office Action issued in IN counterpart Application No. 8789/CHENP/2011, dated Jul. 18, 2017.
Communication dated Apr. 11, 2017, from the Brazil Patent Office in counterpart application No. PI1015413-2.

\* cited by examiner

METHOD FOR PRODUCING MICROCAPSULE

TECHNICAL FIELD

The present invention relates to a method for producing a microcapsule and a microcapsule produced by the method.

BACKGROUND ART

There is known a microcapsule wherein a liquid droplet, in which a pesticidal compound is suspended in a fatty acid ester such as methyl O-acetylricinoleate, is coated with a resin (see US 2009/0142406A1).

SUMMARY OF THE INVENTION

Technical Problem

A microcapsule formulation of a pesticidal compound is a formulation which is intended to control the release timing of the pesticidal compound contained therein.

An object of the present invention is to provide a technique for delaying the release timing of the pesticidal compound with a microcapsule containing a pesticidal compound in a fatty acid ester such as methyl O-acetylricinoleate.

Solution to Problem

The inventors of the present invention have found that the timing of release of the pesticidal compound from the microcapsule is delayed when a microcapsule is produced by using a mixture of a pesticidal compound, a fatty acid ester such as methyl O-acetylricinoleate and a polyisocyanate being kept at 20 to 60° C. for 3 hours or more. The inventors have also found that the microcapsule produced by the production method is excellent in light stability as compared to a conventional microcapsule.

The present invention provides:

[1] A method for producing a microcapsule, which comprises:

(1) keeping a mixture of a pesticidal compound, a compound represented by formula (I) and a polyisocyanate at 20 to 60° C. for 3 hours or more:

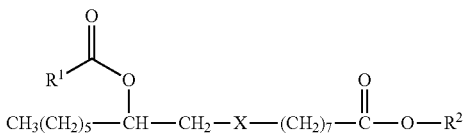

wherein X represents —CH$_2$—CH$_2$— or —CH═CH—, R$^1$ represents a C1-C4 alkyl group, and R$^2$ represents a C1-C4 alkyl group;

(2) then adding the mixture to water containing a polyol or a polyamine, and producing liquid droplets in the water; and (3) forming a film of polyurethane or polyurea around the droplets;

[2] The method according to [1], wherein the weight ratio of the pesticidal compound to the compound represented by formula (I) is from 10:100 to 100:100;

[3] The method according to [1] or [2], wherein the compound represented by formula (I) is a C1-C4 alkyl ester of O-acetylricinoleic acid;

[4] The method according to [1] or [2], wherein the compound represented by formula (I) is methyl O-acetylricinoleate;

[5] The method according to any one of [1] to [4], wherein the pesticidal compound is a solid pesticidal compound;

[6] The method according to any one of [1] to [4], wherein the pesticidal compound is a neonicotinoid compound;

[7] The method according to any one of [1] to [4], wherein the pesticidal compound is clothianidin; and

[8] A microcapsule produced by the method according to any one of [1] to [7].

Effects of the Invention

According to the method for producing a microcapsule of the present invention, a microcapsule from which release of a pesticidal compound is more controlled than that from a conventional microcapsule can be obtained.

DESCRIPTION OF EMBODIMENTS

The method for producing a microcapsule of the present invention comprises the following steps:

step (1) keeping a mixture of a pesticidal compound, a compound represented by formula (I) and a polyisocyanate at 20 to 60° C. for 3 hours or more:

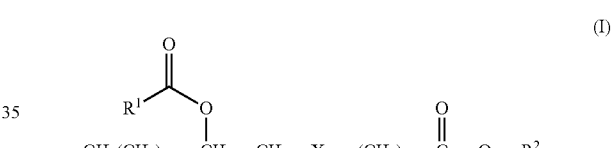

wherein X represents —CH$_2$—CH$_2$— or —CH═CH—, R$^1$ represents a C1-C4 alkyl group, and R$^2$ represents a C1-C4 alkyl group;

step (2) then adding the mixture into water containing a polyol or a polyamine, and producing liquid droplets in the water; and step (3) forming a film of polyurethane or polyurea around the droplets.

In the present invention, the pesticidal compound is preferably a solid pesticidal compound. As used herein, the solid pesticidal compound usually means a compound having pesticidal activity and having a melting point of 15° C. or higher, preferably 50° C. or higher. More preferably, the solid pesticidal compound as used herein is a compound having pesticidal activity whose melting point is 15° C. or higher, preferably 50° C. or higher and whose solubility is 5% by weight or less in the compound represented by the above formula (I).

Examples of the pesticidal compound used in the present invention include an insecticidal compound, a fungicidal compound, a herbicidal compound, an insect growth regulating compound, a plant growth regulating compound, and an insect repelling compound.

Examples of the insecticidal compound include carbamate compounds such as propoxur, isoprocarb, xylylcarb, metolcarb, XMC, carbaryl, pirimicarb, carbofuran, methomyl, fenoxycarb, alanycarb, and metoxadiazone; organophosphorus compounds such as acephate, phenthoate, vamidothion, trichlorfon, monocrotophos, tetrachlorvinphos, dimethylvinphos, phosalone, chlorpyrifos, chlorpyrifos-methyl, pyridaphenthion, quinalphos, methidathion, methamidophos, dimethoate, formothion, azinphos-ethyl, azinphos-methyl, and salithion; neonicotinoid compounds such as imidacloprid, nitenpyram, acetamiprid, clothianidin, and thiamethoxam; 4-chloro-2-(2-chloro-2-methylpropyl)-5-(6-iodo-3-pyridylmethoxy)pyridazine-3 (2H)-one, cartap, buprofezin, thiocyclam, bensultap, fenoxycarb, fenazaquin, fenpyroximate, pyridaben, hydramethylnon, thiodicarb, chlorfenapyr, fenproximate, pymetrozine, pyrimidifen, tebufenozide, tebufenpyrad, triazamate, indoxacarb, sulfluramide, milbemectin, abamectin, and paradichlorobenzene.

Examples of the fungicidal compound include benzimidazole compounds such as benomyl, carbendazim, thiabendazole, and thiophanate-methyl; phenylcarbamate compounds such as diethofencarb; dicarboxylmide compounds such as procymidone, iprodione, and vinclozolin; azole compounds such as diniconazole, propenazole, epokyconazole, tebuconazole, difenoconazole, cyproconazole, flusilazole, and triadimefon; acylalanine compounds such as metalaxyl; carboxyamide compounds such as furametpyr, mepronil, flutolanil, and trifluzamide; organophosphorus compounds such as tolclofos-methyl, fosetyl-aluminum, and pyrazophos; anilinopyrimidine compounds such as pyrimethanil, mepanipyrim, and cyprodinil; cyanopyrrole compounds such as fludioxonil, and fenpiclonil; chlorothalonil, manzeb, captan, folpet, tricyclazole, pyroquilon, probenazole, fthalide, cymoxanil, dimethomorph, famoxadone, oxolinic acid and a salt thereof, fluazinam, ferimzone, diclocymet, chlobenthiazone, isovaledione, tetrachloroisophthalonitrile, thiophthalimide oxybisphenoxyarsine, and 3-iodo-2-propylbutylcarbamate.

Examples of the herbicidal compound include triazine compounds such as atrazine, and metribuzin; urea compounds such as fluometuron, and isoproturon; hydroxybenzonitrile compounds such as bromoxynil, and ioxynil; 2,6-dinitroaniline compounds such as pendimethalin, and trifluralin; aryloxyalkanoic acid compounds and salts thereof such as 2,4-D, dicamba, fluoroxypyr, and mecoprop; sulfonylurea compounds such as bensulfuron-methyl, metsulfuron-methyl, nicosulfuron, primisulfuron-methyl, and cyclosulfamuron; imidazolinone compounds and salts thereof such as imazapyr, imazaquin, and imazethapyr; sulfentrazone, paraquat, flumetsulam, triflusulfuron-methyl, fenoxaprop-p-ethyl, cyhalofop-butyl, diflufenican, norflurazon, isoxaflutole, glufosinate ammonium salts, glyphosate salts, bentazone, benthiocarb, mefenacet, propanil, fluthiamide, flumiclorac-pentyl, and flumioxazin.

Examples of the insect growth regulating compound include benzoylurea compounds such as diflubenzuron, chlorfluazuron, lufenuron, hexaflumuron, flufenoxuron, flucycloxuron, cyromazine, diafenthiuron, hexythiazox, novaluron, teflubenzuron, triflumuron, 1-(2,6-difluorobenzoyl)-3-[2-fluoro-4-(trifluoromethyl)phenyl]urea, 1-(2,6-difluorobenzoyl)-3-[(2-fluoro-4-(1,1,2,3,3,3-hexafluoropropoxy)phenyl]urea, and 1-(2,6-difluorobenzoyl)-3-[2-fluoro-4-(1,1,2,2-tetrafluoroethoxy)phenyl]urea; and pyriproxyfen.

Examples of the plant growth regulating compound include maleic hydrazide, chlormequat, ethephon, gibberellin, mepichat chloride, thidiazuron, inabenfide, paclobutrazol, and uniconazole.

Examples of the insect repelling compound include 1S,3R,4R,6R-carane-3,4-diol, and dipropyl 2,5-pyridinedicarboxylate.

Examples of the C1-C4 alkyl groups represented by $R^1$ or $R^2$ in formula (I), as used herein, include a methyl group, an ethyl group, a propyl group and a butyl group.

The compound represented by formula (I) can be obtained by converting the carboxyl group of ricinoleic acid or 12-hydroxystearic acid into an alkoxycarbonyl group by condensation with a lower alcohol compound, and further converting the hydroxyl group of ricinoleate or 12-hydroxystearate into an acyloxy group by condensation with a lower fatty acid.

Examples of the compound represented by formula (I) include C1-C4 alkyl esters of O-acetylricinoleic acid and C1-C4 alkyl esters of 12-acetoxystearic acid.

More specific examples of the compound represented by formula (I) include:

methyl O-acetylricinoleate [$CH_3$ $(CH_2)_5CH(OCOCH_3)$ $CH_2CH=CH(CH_2)_7CO_2CH_3$]

ethyl O-acetylricinoleate [$CH_3$ $(CH_2)_5CH(OCOCH_3)$ $CH_2CH=CH(CH_2)_7CO_2CH_2CH_3$]

butyl O-acetylricinoleate [$CH_3(CH_2)_5CH(OCOCH_3)$ $CH_2CH=CH(CH_2)_7CO_2(CH_2)_3CH_3$], methyl 12-acetoxysteareate [$CH_3(CH_2)_5CH(OCOCH_3)$ $(CH_2)_{10}CO_2CH_3$], and butyl 12-acetoxysteareate [$CH_3(CH_2)_5CH(OCOCH_3)$ $(CH_2)_{10}CO_2(CH_2)_3CH_3$].

Examples of the polyisocyanate used in the present invention include hexamethylene diisocyanate, an adduct of hexamethylene diisocyanate and trimethylolpropane, a biuret condensate of 3 molecules of hexamethylene diisocyanate, an adduct of tolylene diisocyanate and trimethylolpropane, an isocyanurate condensate of tolylene diisocyanate, an isocyanurate condensate of hexamethylene diisocyanate, an isocyanurate condensate of isophorone diisocyanate, an isocyanate prepolymer in which one isocyanate part of hexamethylene diisocyanate forms an isocyanurate component together with 2 molecules of tolylene diisocyanate and the other isocyanate part forms an isocyanurate component together with 2 molecules of other hexamethylene diisocyanate, 4,4'-methylene bis(cyclohexylisocyanate), and trimethylhexamethylene diisocyanate.

In the present invention, the weight ratio of the pesticidal compound to the compound represented by formula (I), that is, the weight ratio of the pesticidal compound to the compound represented by formula (I) is usually from 10:100 to 100:100, preferably from 20:100 to 40:100.

The amount of the polyisocyanate used in the present invention is usually determined depending on the amount of the film of a microcapsule to be produced. The amount of the film of a microcapsule to be produced is usually from 5 to 45% by weight, preferably from 10 to 30% by weight of the weight of the entire microcapsule. The amount of the polyisocyanate used in the present invention is usually from 25 to 90% by weight, preferably from 40 to 70% by weight of the weight of the film of a microcapsule.

The pesticidal compound is usually dissolved or suspended in the compound represented by formula (I).

When the pesticidal compound is dissolved in the compound represented by formula (I), the mixture of a pesticidal compound, a compound represented by formula (I) and a polyisocyanate used in the step (1) can be prepared by mixing the pesticidal compound, the compound represented by formula (I) and the polyisocyanate.

When the pesticidal compound is a solid pesticidal compound, the solid pesticidal compound suspension in the compound represented by formula (I) may be formed in accordance with the solubility of the solid pesticidal compound in the compound represented by formula (I) and the weight ratio of the solid pesticidal compound to the compound represented by formula (I). When the solid pesticidal compound is suspended in the compound represented by formula (I), the mixture of a pesticidal compound, a compound represented by formula (I) and a polyisocyanate used in the step (1) can be prepared, for example, by grinding the solid pesticidal compound in the compound represented by formula (I) to obtain a suspension and then adding the polyisocyanate into the resultant suspension.

An example of a method for grinding the solid pesticidal compound in the compound represented by formula (I) is a wet grinding method which comprises adding the solid pesticidal compound and, if necessary, beads or the like for grinding to the compound represented by formula (I) and then grinding the mixture with a grinder. Examples of the grinder include mills such as a bead mill, a ball mill and a rod mill, and rotor-stator homogenizers. Specific examples of the mill include Attritor (manufactured by MITSUI MIIKE MACHINERY CO., LTD.), Dyno Mill (manufactured by WILLY A. BACHOFEN AG. MASCHINENFABRIK), Colloid Mill (manufactured by PRIMIX CORP.) and Pearl Mill (manufactured by ASHIZAWA FINETECH, LTD.). Specific examples of the rotor-stator homogenizer include Polytron Homogenizer (manufactured by KINEMATICA AG).

Grinding of the solid pesticidal compound in the compound represented by formula (I) may be attained by 2 or more operations. For grinding the solid pesticidal compound in the compound represented by formula (I), for example, the solid pesticidal compound may be coarsely ground in the first operation and then finely ground in the second operation. An example of a method for grinding the solid pesticidal compound in the compound represented by formula (I) in 2 operations is a method which comprises using a rotor-stator homogenizer for the first operation and using a mill for the second operation.

When the solid pesticidal compound is suspended in the compound represented by formula (I), the particle size of the solid pesticidal compound suspended in the compound represented by formula (I) is usually 10 μm or less, preferably in the range of 1 to 5 μm in terms of volume median diameter. It is preferred that, based on the gross volume of the particles of the solid pesticidal compound suspended in the compound represented by formula (I), the net volume of particles with a diameter of 10 μm or more is 10% or less.

In the present invention, the mixture of a pesticidal compound, a compound represented by formula (I) and a polyisocyanate may further contain an organic solvent. Examples of the organic solvent include aliphatic hydrocarbons such as trimethylpentane, aromatic hydrocarbons such as phenylxylylethane, alkylbenzene and alkylnaphthalene, ethers such as 2-ethylhexyl ether, and vegetable oils such as cotton seed oil. When the mixture contains an organic solvent, the weight ratio of the organic solvent based on the weight of the compound represented by formula (I) is usually ½ or less, preferably ⅜ or less, more preferably ¼ or less.

In the step (1) of the microcapsule production method of the present invention, the mixture of a pesticidal compound, a compound represented by formula (I) and a polyisocyanate thus obtained is kept at 20 to 60° C. for 3 hours or more, preferably at 20 to 40° C. for 5 hours or more.

While the mixture of a pesticidal compound, a compound represented by formula (I) and a polyisocyanate is kept at 20 to 60° C., the mixture may be stirred or allowed to stand. In the step (1), the mixture is usually controlled so as to be kept at 20 to 60° C.

In the step (2) of the microcapsule production method of the present invention, the mixture obtained in the step (1) is added to water containing a polyol or a polyamine, and liquid droplets are produced in the water.

When the water contains a polyol in this step, a microcapsule with a polyurethane film is produced. When the water contains a polyamine in this step, a microcapsule with a polyurea film is produced.

The water containing a polyol can be prepared, for example, by mixing water and a polyol. The water containing a polyamine can be prepared, for example, by mixing water and a polyamine or a polyamine salt.

Examples of the polyol as used herein include ethylene glycol, propylene glycol, butylene glycol, and cyclopropylene glycol. Examples of the polyamine as used herein include ethylenediamine, hexamethylenediamine, diethyltriamine, and triethylenetetramine.

The amount of the polyol or polyamine used in the present invention is usually determined depending on the amount of the film of a microcapsule to be produced. The amount of the polyol used in the present invention is usually from 5 to 80% by weight, preferably from 20 to 60% by weight of the amount of the film of a microcapsule. The amount of the polyamine used in the present invention is usually from 5 to 80% by weight, preferably from 20 to 60% by weight of the amount of the film of a microcapsule.

The weight ratio of water used in the step (2) is usually in a range from 0.8 to 2 times the weight of the mixture obtained in the step (1). As water used in the step (2), deionized water is preferably used. Water used in the step (2) may contain a thickening agent, if necessary.

Examples of the thickening agent include natural polysaccharides such as xanthan gum, rhamsan gum, locust bean gum, carrageenan, welan gum and gum arabic; synthetic polymers such as sodium polyacrylate; semi-synthetic polymers such as carboxymethyl cellulose; mineral powders such as aluminum magnesium silicate, smectite, bentonite, hectorite and fumed silica; and alumina sol.

An example of a method for preparing liquid droplets in water in the step (2) is a method which comprises adding the mixture obtained in the step (1) to water containing a polyol or a polyamine and then stirring the resultant mixture with a stirrer. Examples of the stirrer used in this operation include a propeller stirrer, a turbine stirrer and a high-speed shear stirrer. Specific examples of the stirrer include T.K. Homo Mixer, T.K. Homomic Line flow, T.K. Pipeline Homo Mixer, and T.K. Fill Mix (manufactured by PRIMIX CORP); Clearmix (manufactured by M TECHNIQUE CO., LTD.); Polytron Homogenizer and Megatron Homogenizer (manufactured by KINEMATICA); and Supraton (manufactured by TSUKISHIMA KIKAI CO., LTD.).

The particle size of microcapsules finally produced by the method of the present invention is almost identical to that of the liquid droplets prepared in the step (2). The liquid droplets prepared in the step (2) and the microcapsules finally produced by the method of the present invention have a particle diameter of usually in the range of 1 to 80 μm, preferably 5 to 50 μm in terms of volume median diameter.

The liquid droplets existing in water obtained in the step (2) are made of a solution of a polyisocyanate in a compound represented by formula (I). The polyisocyanate contained in the liquid droplets is polymerized with the polyol or polyamine existing in the water at the interfaces between the liquid droplets and the water. As a result, a polyurethane or polyurea film is formed around the liquid droplets to give an aqueous suspension of microcapsules.

For the polyurethane film, the film of polyurethane resin is formed around the liquid droplets, for example, by heating a water dispersion of the liquid droplets prepared in the step (2) to 40 to 80° C. and then keeping the dispersion at the same temperature for about 0.5 to 48 hours while stirring. For the polyurea film, the film of polyurea resin is formed around the liquid droplets, for example, by adjusting a water dispersion of the liquid droplets prepared in the step (2) to a neutral to weak alkaline pH and then keeping the dispersion at 0 to 50° C. for about 0.5 to 48 hours.

According to the method as described above, a microcapsule is produced in the form of a water suspension.

The water suspension of the microcapsule thus produced can be subjected to centrifugation, filtration or spray drying to obtain a powder formulation of the microcapsule.

To the water suspension of the microcapsule produced by the method as described above, a thickening agent, an antifreezing agent, a preservative, a density regulator, a pH regulator or water can be further added. In this case, the microcapsule thus produced can be used, for example, as a water suspended pesticidal composition containing 0.1 to 30% by weight of a pesticidal compound.

Examples of the thickening agent include those described above. Examples of the antifreezing agent include propylene glycol. Examples of the preservative include p-hydroxybenzoic acid esters; isothiazoline derivatives such as 5-chloro-2-methyl-4-isothiazolin-3-one and 2-methyl-4-isothiazolin-3-one; 2-bromo-2-nitropropane-1,3-diol; and salicylic acid derivatives. Specific examples of the preservative include Biohope L (manufactured by K.I. CHEMICAL INDUSTRY CO., LTD.) and Proxel GXL (manufactured by Avecia K.K.). Examples of the density ragulator include water-soluble salts such as sodium sulfate and water-soluble compounds such as urea. Examples of the pH regulator include disodium hydrogen phosphate, dipotassium hydrogen phosphate and sodium hydroxide.

When the pesticidal compound is an insecticidal compound, a pesticidal composition containing the microcapsule of the present invention is sprayed on pests or habitats of pests in an amount of about 0.1 to 1,000 g/1,000 m², preferably about 1 to 100 g/1,000 m² of the pesticidal compound.

Examples of a microcapsule produced by the method of the present invention are shown below.

A microcapsule produced by a method for producing a microcapsule which comprises keeping a mixture of a pesticidal compound, a compound represented by formula (I) and a polyisocyanate at 20 to 60° C. for 3 hours or more:

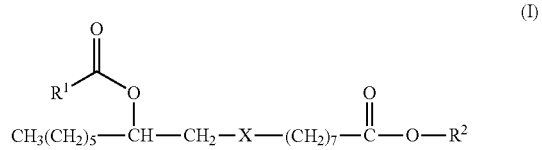

(I)

wherein X represents —CH₂—CH₂— or —CH=CH—, R¹ represents a C1-C4 alkyl group, and R² represents a C1-C4 alkyl group; then adding the mixture to water containing a polyol or a polyamine, and producing liquid droplets in the water; and then forming a film of polyurethane or polyurea around the droplets (hereinafter, referred to as the present microcapsule).

The present microcapsule, wherein the net volume of microcapsule particles with a particle diameter of 5 μm or less is less than 20% based on the gross volume of microcapsule particles and the net volume of microcapsule particles with a particle diameter of 50 μm or more is less than 20% based on the gross volume of microcapsule particles.

The present microcapsule, wherein the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, and the ratio of volume median diameter/film thickness is from 25 to 150.

The present microcapsule, wherein the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, and the film is made of polyurethane.

The present microcapsule, wherein the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, the ratio of volume median diameter/film thickness is from 25 to 150, and the film is made of polyurethane.

The present microcapsule, wherein the weight ratio of the pesticidal compound to the compound represented by formula (I) is from 20:100 to 40:100, the net volume of microcapsule particles with a particle diameter of 5 μm or less is less than 20% based on the gross volume of microcapsule particles, and the net volume of microcapsule particles with a particle diameter of 50 μm or more is less than 20% based on the gross volume of microcapsule particles.

The present microcapsule, wherein the weight ratio of the pesticidal compound to the compound represented by formula (I) is from 20:100 to 40:100, the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, and the ratio of volume median diameter/film thickness is from 25 to 150.

The present microcapsule, wherein the weight ratio of the pesticidal compound to the compound represented by formula (I) is from 20:100 to 40:100, the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, and the film is made of polyurethane.

The present microcapsule, wherein the weight ratio of the pesticidal compound to the compound represented by formula (I) is from 20:100 to 40:100, the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, the ratio of volume median diameter/film thickness is from 25 to 150, and the film is made of polyurethane.

The present microcapsule, which contains an isothiazoline derivative as a preservative, and wherein the net volume of microcapsule particles with a particle diameter of 5 μm or less is less than 20% based on the gross volume of microcapsule particles and the net volume of microcapsule particles with a particle diameter of 50 μm or more is less than 20% based on the gross volume of microcapsule particles.

The present microcapsule, which contains an isothiazoline derivative as a preservative, and wherein the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, and the ratio of volume median diameter/film thickness is from 25 to 150.

The present microcapsule, which contains an isothiazoline derivative as a preservative, and wherein the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, and the film is made of polyurethane.

The present microcapsule, which contains an isothiazoline derivative as a preservative, and wherein the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, the ratio of volume median diameter/film thickness is from 25 to 150, and the film is made of polyurethane.

The present microcapsule, which contains an isothiazoline derivative as a preservative, and wherein the weight ratio of the pesticidal compound to the compound represented by formula (I) is from 20:100 to 40:100, the net volume of microcapsule particles with a particle diameter of 5 μm or less is less than 20% based on the gross volume of microcapsule particles, and the net volume of microcapsule particles with a particle diameter of 50 μm or more is less than 20% based on the gross volume of microcapsule particles.

The present microcapsule, which contains an isothiazoline derivative as a preservative, and wherein the weight ratio of the pesticidal compound to the compound represented by formula (I) is from 20:100 to 40:100, the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, and the ratio of volume median diameter/film thickness is from 25 to 150.

The present microcapsule, which contains an isothiazoline derivative as a preservative, and wherein the weight ratio of the pesticidal compound to the compound represented by formula (I) is from 20:100 to 40:100, the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, and the film is made of polyurethane.

The present microcapsule, which contains an isothiazoline derivative as a preservative, and wherein the weight ratio of the pesticidal compound to the compound represented by formula (I) is from 20:100 to 40:100, the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, the ratio of volume median diameter/film thickness is from 25 to 150, and the film is made of polyurethane.

The present microcapsule, which contains a pH regulator and an isothiazoline derivative as a preservative, and wherein the net volume of microcapsule particles with a particle diameter of 5 μm or less is less than 20% based on the gross volume of microcapsule particles and the net volume of microcapsule particles with a particle diameter of 50 μm or more is less than 20% based on the gross volume of microcapsule particles.

The present microcapsule, which contains a pH regulator and an isothiazoline derivative as a preservative, and wherein the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, and the ratio of volume median diameter/film thickness is from 25 to 150.

The present microcapsule, which contains a pH regulator and an isothiazoline derivative as a preservative, and wherein the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, and the film is made of polyurethane.

The present microcapsule, which contains a pH regulator and an isothiazoline derivative as a preservative, and wherein the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, the ratio of volume median diameter/film thickness is from 25 to 150, and the film is made of polyurethane.

The present microcapsule, which contains a pH regulator and an isothiazoline derivative as a preservative, and wherein the weight ratio of the pesticidal compound to the compound represented by formula (I) is from 20:100 to 40:100, the net volume of microcapsule particles with a particle diameter of 5 μm or less is less than 20% based on the gross volume of microcapsule particles, and the net volume of microcapsule particles with a particle diameter of 50 μm or more is less than 20% based on the gross volume of microcapsule particles.

The present microcapsule, which contains a pH regulator and an isothiazoline derivative as a preservative, and wherein the weight ratio of the pesticidal compound to the compound represented by formula (I) is from 20:100 to 40:100, the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, and the ratio of volume median diameter/film thickness is from 25 to 150.

The present microcapsule, which contains a pH regulator and an isothiazoline derivative as a preservative, and wherein the weight ratio of the pesticidal compound to the compound represented by formula (I) is from 20:100 to 40:100, the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, and the film is made of polyurethane.

The present microcapsule, which contains a pH regulator and an isothiazoline derivative as a preservative, and wherein the weight ratio of the pesticidal compound to the compound represented by formula (I) is from 20:100 to 40:100, the net volume of microcapsule particles with a particle diameter of 5 μm or less is less than 20% based on the gross volume of microcapsule particles, the net volume of microcapsule particles with a particle diameter of 50 μm or more is less than 20% based on the gross volume of microcapsule particles, the ratio of volume median diameter/film thickness is from 25 to 150, and the film is made of polyurethane.

EXAMPLES

Hereinafter, the present invention will be described in more detail by way of production examples and test examples, which the present invention is not limited to.

Production Example 1

250 g of clothianidin and 750 g of methyl O-acetylricinoleate (Ricsizer C-101, manufactured by Itoh Oil Chemicals Co., Ltd., content: 95.5%) were mixed (the resultant mixture is referred to as the mixture 1-1). The mixture 1-1 was stirred with a rotor-stator homogenizer (Polytron Homogenizer, manufactured by KINEMATICA AG) to grind clothianidin contained in the mixture 1-1 for about 10 minutes (the resultant mixture is referred to as the mixture 1-2). The clothianidin particles in the mixture 1-2 had a volume median diameter of 0.5 mm.

The mixture 1-2 was fed into Dyno Mill (manufactured by WILLY A. BACHOFEN AG. MASCHINENFABRIK, vessel size: 600 mL, filled with 1,150 g of spherical glass of 1 mm diameter, revolution speed of impeller: 12 m/sec as a peripheral speed) at a rate of 3 L/hr to further grind the clothianidin particles (the resultant mixture is referred to as the mixture 1-3). The clothianidin particles in the mixture 1-3 had a volume median diameter of 2.4 μm, wherein the net volume of the particles with a diameter of 10 μm or more was 1.6% based on the gross volume of microcapsule particles.

To 100 g of the mixture 1-3 was added 21.6 g of a polyisocyanate (Sumidur L-75, adduct of trimethylolpropane and toluenediisocyanate, manufactured by SUMIKA BAYER URETHANE CO., LTD.) at 20° C. (the resultant mixture is referred to as the mixture 1-4). The mixture 1-4 was kept at 20° C. for 24 hours (the resultant mixture is referred to as the mixture 1-5).

To 108.8 g of water (deionized water) were added 12.4 g of ethylene glycol and 12.6 g of gum arabic (Arabic Cole SS manufactured by SAN-EI YAKUHIN BOEKI CO., LTD.) to prepare an aqueous phase. All of the aqueous phase and all of the mixture 1-5 were mixed (the resultant mixture is referred to as the mixture 1-6).

The mixture 1-6 was stirred with a homogenizer (T.K. Autohomomixer, manufactured by PRIMIX CORP., revolution speed: 9,000 rpm) at room temperature to form liquid droplets in water (the resultant mixture is referred to as the mixture 1-7).

The mixture 1-7 was stirred at 60° C. for 24 hours to give an aqueous suspension composition of clothianidin microcapsules (hereinafter, referred to as the aqueous suspension composition 1).

The resultant microcapsules had a volume median diameter of 20.9 μm, wherein the net volume of the microcapsules with a particle diameter of 5 μm or less was 8.9% based on the gross volume of microcapsule particles, and the net volume of the microcapsules with a particle diameter of 50 μm or more was 0% based on the gross volume of microcapsule particles.

Production Example 2

250 g of clothianidin and 750 g of methyl O-acetylricinoleate (Ricsizer C-101, manufactured by Itoh Oil Chemicals Co., Ltd., content: 95.5%) were mixed (the resultant mixture is referred to as the mixture 2-1). The mixture 2-1 was stirred with a rotor-stator homogenizer (Polytron Homogenizer, manufactured by KINEMATICA AG) to grind clothianidin contained in the mixture 2-1 for about 10 minutes (the resultant mixture is referred to as the mixture 2-2). The clothianidin particles in the mixture 2-2 had a volume median diameter of 0.5 mm.

The mixture 2-2 was fed into Dyno Mill (manufactured by WILLY A. BACHOFEN AG. MASCHINENFABRIK, vessel size: 600 mL, filled with 1,150 g of spherical glass of 1 mm diameter, revolution speed of impeller: 12 m/sec as a peripheral speed) at a rate of 3 L/hr to further grind the clothianidin particles (the resultant mixture is referred to as the mixture 2-3). The clothianidin particles in the mixture 2-3 had a volume median diameter of 2.7 μm, wherein the net volume of the particles with a diameter of 10 μm or more was 1.9% based on the gross volume of microcapsule particles.

To 100 g of the mixture 2-3 was added 21.6 g of a polyisocyanate (Sumidur L-75, adduct of trimethylolpropane and toluenediisocyanate, manufactured by SUMIKA BAYER URETHANE CO., LTD.) at 40° C. (the resultant mixture is referred to as the a mixture 2-4). The mixture 2-4 was kept at 40° C. for 5 hours (the resultant mixture is referred to as the mixture 2-5).

To 108.8 g of water (deionized water) were added 12.4 g of ethylene glycol and 12.6 g of gum arabic (Arabic Cole SS manufactured by SAN-EI YAKUHIN BOEKI CO., LTD.) to prepare an aqueous phase. All of the aqueous phase and all of the mixture 2-5 were mixed (the resultant mixture is referred to as the mixture 2-6).

The mixture 2-6 was stirred with a homogenizer (T.K. Autohomomixer, manufactured by PRIMIX CORP., revolution speed: 9,000 rpm) at room temperature to form liquid droplets in water (the resultant mixture is referred to as the mixture 2-7).

The mixture 2-7 was stirred at 60° C. for 24 hours to give an aqueous suspension composition of clothianidin microcapsules (hereinafter, referred to as the aqueous suspension composition 2).

The resultant microcapsules had a volume median diameter of 17.7 μm, wherein the net volume of the microcapsules with a particle diameter of 5 μm or less was 11.6% based on the gross volume of microcapsule particles, and the net volume of the microcapsules with a particle diameter of 50 μm or more was 0% based on the gross volume of microcapsule particles.

Production Example 3

250 g of clothianidin and 750 g of methyl O-acetylricinoleate (Ricsizer C-101, manufactured by Itoh Oil Chemicals Co., Ltd., content: 95.5%) were mixed (the resultant mixture is referred to as the mixture 3-1). The mixture 3-1 was stirred with a rotor-stator homogenizer (Polytron Homogenizer, manufactured by KINEMATICA AG) to grind clothianidin contained in the mixture 3-1 for about 10 minutes (the resultant mixture is referred to as the mixture 3-2). The clothianidin particles in the mixture 3-2 had a volume median diameter of 0.5 mm.

The mixture 3-2 was fed into Dyno Mill (manufactured by WILLY A. BACHOFEN AG. MASCHINENFABRIK, vessel size: 600 mL, filled with 1,150 g of spherical glass of 1 mm diameter, revolution speed of impeller: 12 m/sec as a peripheral speed) at a rate of 3 L/hr to further grind the clothianidin particles (the resultant mixture is referred to as the mixture 3-3). The clothianidin particles in the mixture 3-3 had a volume median diameter of 2.5 µm, wherein the net volume of the particles with a diameter of 10 µm or more was 1.8% based on the gross volume of microcapsule particles.

To 100 g of the mixture 3-3 was added 21.6 g of a polyisocyanate (Sumidur L-75, adduct of trimethylolpropane and toluenediisocyanate, manufactured by SUMIKA BAYER URETHANE CO., LTD.) at 30° C. (the resultant mixture is referred to as the mixture 3-4). The mixture 3-4 was kept at 30° C. for 20 hours (the resultant mixture is referred to as the mixture 3-5).

To 108.8 g of water (deionized water) were added 12.4 g of ethylene glycol and 12.6 g of gum arabic (Arabic Cole SS manufactured by SAN-EI YAKUHIN BOEKI CO., LTD.) to prepare an aqueous phase. All of the aqueous phase and all of the mixture 3-5 were mixed (the resultant mixture is referred to as the mixture 3-6).

The mixture 3-6 was stirred with a homogenizer (T.K. Autohomomixer, manufactured by PRIMIX CORP., revolution speed: 9,000 rpm) at room temperature to form liquid droplets in water (the resultant mixture is referred to as the mixture 3-7).

The mixture 3-7 was stirred at 60° C. for 24 hours to give an aqueous suspension composition of clothianidin microcapsules (hereinafter, referred to as the aqueous suspension composition 3).

The resultant microcapsules had a volume median diameter of 22.5 µm, wherein the net volume of the microcapsules with a diameter of 5 µm or less was 7.9% based on the gross volume of microcapsule particles, and the net volume of the microcapsules with a diameter of 50 µm or more was 0.4% based on the gross volume of microcapsule particles.

Production Example 4

250 g of clothianidin and 750 g of methyl O-acetylricinoleate (Ricsizer C-101, manufactured by Itoh Oil Chemicals Co., Ltd., content: 95.5%) were mixed (the resultant mixture is referred to as the mixture 4-1). The mixture 4-1 was stirred with a rotor-stator homogenizer (Polytron Homogenizer, manufactured by KINEMATICA AG) to grind clothianidin contained in the mixture 4-1 for about 10 minutes (the resultant mixture is referred to as the mixture 4-2). The clothianidin particles in the mixture 4-2 had a volume median diameter of 0.5 mm.

The mixture 4-2 was fed into Dyno Mill (manufactured by WILLY A. BACHOFEN AG. MASCHINENFABRIK, vessel size: 600 mL, filled with 1,150 g of spherical glass of 1 mm diameter, revolution speed of impeller: 12 m/sec as a peripheral speed) at a rate of 3 L/hr to further grind the clothianidin particles (the resultant mixture is referred to as the mixture 4-3). The clothianidin particles in the mixture 4-3 had a volume median diameter of 2.5 µm, wherein the net volume of the particles with a diameter of 10 µm or more was 1.8% based on the gross volume of microcapsule particles.

To 100 g of the mixture 4-3 was added 9.8 g of a polyisocyanate (Sumidur L-75, adduct of trimethylolpropane and toluenediisocyanate, manufactured by SUMIKA BAYER URETHANE CO., LTD.) was added at 40° C. (the resultant mixture is referred to as the mixture 4-4). The mixture 4-4 was kept at 40° C. for 20 hours (the resultant mixture is referred to as the mixture 4-5).

To 108.8 g of water (deionized water) were added 5.6 g of ethylene glycol and 12.6 g of gum arabic (Arabic Cole SS manufactured by SAN-EI YAKUHIN BOEKI CO., LTD.) to prepare an aqueous phase. All of the aqueous phase and all of the mixture 4-5 were mixed (the resultant mixture is referred to as the mixture 4-6).

The mixture 4-6 was stirred with a homogenizer (T.K. Autohomomixer, manufactured by PRIMIX CORP., revolution speed: 9,000 rpm) at room temperature to form liquid droplets in water (the resultant mixture is referred to as the mixture 4-7).

The mixture 4-7 was stirred at 60° C. for 24 hours to give an aqueous suspension composition of clothianidin microcapsules (hereinafter, referred to as the aqueous suspension composition 4).

The resultant microcapsules had a volume median diameter of 19.8 µm, wherein the net volume of the microcapsules with a diameter of 5 µm or less was 9.4% based on the gross volume of microcapsule particles, and the net volume of the microcapsules with a diameter of 50 µm or more was 0.4% based on the gross volume of microcapsule particles.

Production Example 5

250 g of clothianidin and 750 g of methyl O-acetylricinoleate (Ricsizer C-101, manufactured by Itoh Oil Chemicals Co., Ltd., content: 95.5%) were mixed (the resultant mixture is referred to as the mixture 5-1). The mixture 5-1 was stirred with a rotor-stator homogenizer (Polytron Homogenizer, manufactured by KINEMATICA AG) to grind clothianidin contained in the mixture 5-1 for about 10 minutes (the resultant mixture is referred to as the mixture 5-2). The clothianidin particles in the mixture 5-2 had a volume median diameter of 0.5 mm.

The mixture 5-2 was fed into Dyno Mill (manufactured by WILLY A. BACHOFEN AG. MASCHINENFABRIK, vessel size: 600 mL, filled with 1,150 g of spherical glass of 1 mm diameter, revolution speed of impeller: 12 m/sec as a peripheral speed) at a rate of 3 L/hr to further grind the clothianidin particles (the resultant mixture is referred to as the mixture 5-3). The clothianidin particles in the mixture 5-3 had a volume median diameter of 2.9 µm, wherein the net volume of the particles with a diameter of 10 µm or more was 3.4% based on the gross volume of microcapsule particles.

To 100 g of the mixture 5-3 was added 21.6 g of a polyisocyanate (Sumidur L-75, adduct of trimethylolpropane and toluenediisocyanate, manufactured by SUMIKA BAYER URETHANE CO., LTD.) at 40° C. (the resultant mixture is referred to as the mixture 5-4). The mixture 5-4 was kept at 40° C. for 10 hours (the resultant mixture is referred to as the mixture 5-5).

To 108.8 g of water (deionized water) were added 12.4 g of ethylene glycol and 12.6 g of gum arabic (Arabic Cole SS manufactured by SAN-EI YAKUHIN BOEKI CO., LTD.) to prepare an aqueous phase. All of the aqueous phase and all of the mixture 5-5 were mixed (the resultant mixture is referred to as the mixture 5-6).

The mixture 5-6 was stirred with a homogenizer (T.K. Autohomomixer, manufactured by PRIMIX CORP., revolution speed: 9,000 rpm) at room temperature to form liquid droplets in water (the resultant mixture is referred to as the mixture 5-7).

The mixture 5-7 was stirred at 60° C. for 24 hours to give an aqueous suspension composition of clothianidin microcapsules (hereinafter, referred to as the aqueous suspension composition 5).

The resultant microcapsules had a volume median diameter of 19.6 µm, wherein the net volume of the microcapsules with a diameter of 5 µm or less was 9.1% based on the gross volume of microcapsule particles, and the net volume of the microcapsules with a diameter of 50 µm or more was 0.3% based on the gross volume of microcapsule particles.

Production Example 6

250 g of clothianidin and 750 g of methyl O-acetylricinoleate (Ricsizer C-101, manufactured by Itoh Oil Chemicals Co., Ltd., content: 95.5%) were mixed (the resultant mixture is referred to as the mixture 6-1). The mixture 6-1 was stirred with a rotor-stator homogenizer (Polytron Homogenizer, manufactured by KINEMATICA AG) to grind clothianidin contained in the mixture 6-1 for about 10 minutes (the resultant mixture is referred to as the mixture 6-2). The clothianidin particles in the mixture 6-2 had a volume median diameter of 0.5 mm.

The mixture 6-2 was fed into Dyno Mill (manufactured by WILLY A. BACHOFEN AG. MASCHINENFABRIK, vessel size: 600 mL, filled with 1,150 g of spherical glass of 1 mm diameter, revolution speed of impeller: 12 m/sec as a peripheral speed) at a rate of 3 L/hr to further grind the clothianidin particles (the resultant mixture is referred to as the mixture 6-3). The clothianidin particles in the mixture 6-3 had a volume median diameter of 2.9 µm, wherein the net volume of the particles with a diameter of 10 µm or more was 3.4% based on the gross volume of microcapsule particles.

To 100 g of the mixture 6-3 was added 21.6 g of a polyisocyanate (Sumidur L-75, adduct of trimethylolpropane and toluenediisocyanate, manufactured by SUMIKA BAYER URETHANE CO., LTD.) at 60° C. (the resultant mixture is referred to as the mixture 6-4). The mixture 6-4 was kept at 60° C. for 3 hours (the resultant mixture is referred to as the mixture 6-5).

To 108.8 g of water (deionized water) were added 12.4 g of ethylene glycol and 12.6 g of gum arabic (Arabic Cole SS manufactured by SAN-EI YAKUHIN BOEKI CO., LTD.) to prepare an aqueous phase. All of the aqueous phase and all of the mixture 6-5 were mixed (the resultant mixture is referred to as the mixture 6-6).

The mixture 6-6 was stirred with a homogenizer (T.K. Autohomomixer, manufactured by PRIMIX CORP., revolution speed: 9,000 rpm) at room temperature to form liquid droplets in water (the resultant mixture is referred to as the mixture 6-7).

The mixture 6-7 was stirred at 60° C. for 24 hours to give an aqueous suspension composition of clothianidin microcapsules (hereinafter, referred to as the aqueous suspension composition 6).

The resultant microcapsules had a volume median diameter of 21.9 µm, wherein the net volume of the microcapsules with a diameter of 5 µm or less was 8.6% based on the gross volume of microcapsule particles, and the net volume of the microcapsules with a diameter of 50 µm or more was 0.1% based on the gross volume of microcapsule particles.

Production Example 7

250 g of clothianidin and 750 g of methyl O-acetylricinoleate (Ricsizer C-101, manufactured by Itoh Oil Chemicals Co., Ltd., content: 95.5%) were mixed (the resultant mixture is referred to as the mixture 7-1). The mixture 7-1 was stirred with a rotor-stator homogenizer (Polytron Homogenizer, manufactured by KINEMATICA AG) to grind clothianidin contained in the mixture 7-1 for about 10 minutes (the resultant mixture is referred to as the mixture 7-2). The clothianidin particles in the mixture 7-2 had a volume median diameter of 0.4 mm.

The mixture 7-2 was fed into Dyno Mill (manufactured by WILLY A. BACHOFEN AG. MASCHINENFABRIK, vessel size: 600 mL, filled with 1,150 g of spherical glass of 1 mm diameter, revolution speed of impeller: 12 m/sec as a peripheral speed) at a rate of 3 L/hr to further grind the clothianidin particles (the resultant mixture is referred to as the mixture 7-3). The clothianidin particles in the mixture 7-3 had a volume median diameter of 2.5 µm, wherein the net volume of the particles with a diameter of 10 µm or more wad 1.8% based on the gross volume of microcapsule particles.

To 100 g of the mixture 7-3 was added 21.6 g of a polyisocyanate (Sumidur L-75, adduct of trimethylolpropane and toluenediisocyanate, manufactured by SUMIKA BAYER URETHANE CO., LTD.) at 25° C. (the resultant mixture is referred to as the mixture 7-4). The mixture 7-4 was kept at 25° C. for 20 hours (the resultant mixture is referred to as the mixture 7-5).

To 108.8 g of water (deionized water) were added 12.4 g of ethylene glycol and 12.6 g of gum arabic (Arabic Cole SS manufactured by SAN-EI YAKUHIN BOEKI CO., LTD.) to prepare an aqueous phase. All of the aqueous phase and all of the mixture 7-5 were mixed (the resultant mixture is referred to as the mixture 7-6).

The mixture 7-6 was stirred with a homogenizer (T.K. Autohomomixer, manufactured by PRIMIX CORP., revolution speed: 11,000 rpm) at room temperature to form liquid droplets in water (the resultant mixture is referred to as the mixture 7-7).

The mixture 7-7 was stirred at 60° C. for 24 hours to give an aqueous suspension composition of clothianidin microcapsules (hereinafter, referred to as the aqueous suspension composition 7).

The resultant microcapsules had a volume median diameter of 13.6 µm, wherein the net volume of the microcapsules with a diameter of 5 µm or less was 15.9% based on the gross volume of microcapsule particles, and the net volume of the microcapsules with a diameter of 50 µm or more was 0% based on the gross volume of microcapsule particles.

Production Example 8

250 g of clothianidin and 750 g of methyl O-acetylricinoleate (Ricsizer C-101, manufactured by Itoh Oil Chemicals Co., Ltd., content: 95.5%) were mixed (the resultant mixture is referred to as the mixture 8-1). The mixture 8-1 was stirred with a rotor-stator homogenizer (Polytron Homogenizer, manufactured by KINEMATICA AG) to grind clothianidin contained in the mixture 8-1 for about 10 minutes (the resultant mixture is referred to as the mixture 8-2). The clothianidin particles in the mixture 8-2 had a volume median diameter of 0.4 mm.

The mixture 8-2 was fed into Dyno Mill (manufactured by WILLY A. BACHOFEN AG. MASCHINENFABRIK, vessel size: 600 mL, filled with 1,150 g of spherical glass of 1 mm diameter, revolution speed of impeller: 12 m/sec as a peripheral speed) at a rate of 3 L/hr to further grind the clothianidin particles (the resultant mixture is referred to as the mixture 8-3). The clothianidin particles in the mixture 8-3 had a volume median diameter of 2.5 µm, wherein the net volume of the particles with a diameter of 10 µm or more was 1.8% based on the gross volume of microcapsule particles.

To 100 g of the mixture 8-3 was added 21.6 g of a polyisocyanate (Sumidur L-75, adduct of trimethylolpropane and toluenediisocyanate, manufactured by SUMIKA BAYER URETHANE CO., LTD.) at 25° C. (the resultant mixture is referred to as the mixture 8-4). The mixture 8-4 was kept at 25° C. for 20 hours (the resultant mixture is referred to as the mixture 8-5).

To 108.8 g of water (deionized water) were added 12.4 g of ethylene glycol and 12.6 g of gum arabic (Arabic Cole SS manufactured by SAN-EI YAKUHIN BOEKI CO., LTD.) to prepare an aqueous phase. All of the aqueous phase and all of the mixture 8-5 were mixed (the resultant mixture is referred to as the mixture 8-6).

The mixture 8-6 was stirred with a homogenizer (T.K. Autohomomixer, manufactured by PRIMIX CORP., revolution speed: 7,000 rpm) at room temperature to form liquid droplets in water (the resultant mixture is referred to as the mixture 8-7).

The mixture 8-7 was stirred at 60° C. for 24 hours to give an aqueous suspension composition of clothianidin microcapsules (hereinafter, referred to as the aqueous suspension composition 8).

The resultant microcapsules had a volume median diameter of 34.9 µm, wherein the net volume of the microcapsules with a diameter of 5 µm or less was 0% based on the gross volume of microcapsule particles, and the net volume of the microcapsules with a particle diameter of 50 µm or more was 16.9% based on the gross volume of microcapsule particles.

Production Example 9

375 g of clothianidin and 750 g of methyl O-acetylricinoleate (Ricsizer C-101, manufactured by Itoh Oil Chemicals Co., Ltd., content: 95.5%) were mixed (the resultant mixture is referred to as the mixture 9-1). The mixture 9-1 was stirred with a rotor-stator homogenizer (Polytron Homogenizer, manufactured by KINEMATICA AG) to grind clothianidin contained in the mixture 9-1 for about 10 minutes (the resultant mixture is referred to as the mixture 9-2). The clothianidin particles in the mixture 9-2 had a volume median diameter of 0.6 mm.

The mixture 9-2 was fed into Dyno Mill (manufactured by WILLY A. BACHOFEN AG. MASCHINENFABRIK, vessel size: 600 mL, filled with 1,150 g of spherical glass of 1 mm diameter, revolution speed of impeller: 12 m/sec as a peripheral speed) at a rate of 3 L/hr to further grind the clothianidin particles (the resultant mixture is referred to as the mixture 9-3). The clothianidin particles in the mixture 9-3 had a volume median diameter of 2.0 µm, wherein the net volume of the particles with a diameter of 10 µm or more was 0% based on the gross volume of microcapsule particles.

To 100 g of the mixture 9-3 was added 21.6 g of a polyisocyanate (Sumidur L-75, adduct of trimethylolpropane and toluenediisocyanate, manufactured by SUMIKA BAYER URETHANE CO., LTD.) at 25° C. (the resultant mixture is referred to as the mixture 9-4). The mixture 9-4 was kept at 25° C. for 20 hours (the resultant mixture is referred to as the mixture 9-5).

To 108.8 g of water (deionized water) were added 12.4 g of ethylene glycol and 12.6 g of gum arabic (Arabic Cole SS manufactured by SAN-EI YAKUHIN BOEKI CO., LTD.) to prepare an aqueous phase. All of the aqueous phase and all of the mixture 9-5 were mixed (the resultant mixture is referred to as the mixture 9-6).

The mixture 9-6 was stirred with a homogenizer (T.K. Autohomomixer, manufactured by PRIMIX CORP., revolution speed: 9,000 rpm) at room temperature to form liquid droplets in water (the resultant mixture is referred to as the mixture 9-7).

The mixture 9-7 was stirred at 60° C. for 24 hours to give an aqueous suspension composition of clothianidin microcapsules (hereinafter, referred to as the an aqueous suspension composition 9).

The resultant microcapsules had a volume median diameter of 18.4 µm, wherein the net volume of the microcapsules with a particle diameter of 5 µm or less was 11.2% based on the gross volume of microcapsule particles, and the net volume of the microcapsules with s particle diameter of 50 µm or more was 0% based on the gross volume of microcapsule particles.

Production Example 10

150 g of clothianidin and 750 g of methyl O-acetylricinoleate (Ricsizer C-101, manufactured by Itoh Oil Chemicals Co., Ltd., content: 95.5%) were mixed (the resultant mixture is referred to as the mixture 10-1). The mixture 10-1 was stirred with a rotor-stator homogenizer (Polytron Homogenizer, manufactured by KINEMATICA AG) to grind clothianidin contained in the mixture 10-1 for about 10 minutes (the resultant mixture is referred to as the mixture 10-2). The clothianidin particles in the mixture 10-2 had a volume median diameter of 0.4 mm.

The mixture 10-2 was fed into Dyno Mill (manufactured by WILLY A. BACHOFEN AG. MASCHINENFABRIK, vessel size: 600 mL, filled with 1,150 g of spherical glass of 1 mm diameter, revolution speed of impeller: 12 m/sec as a peripheral speed) at a rate of 3 L/hr to further grind the clothianidin particles (the resultant mixture is referred to as the mixture 10-3). The clothianidin particles in the mixture 10-3 had a volume median diameter of 2.9 µm, wherein the net volume of the particles with a diameter of 10 µm or more was 3.3% based on the gross volume of microcapsule particles.

To 100 g of the mixture 10-3 was added 21.6 g of a polyisocyanate (Sumidur L-75, adduct of trimethylolpropane and toluenediisocyanate, manufactured by SUMIKA BAYER URETHANE CO., LTD.) at 25° C. (the resultant mixture is referred to as the mixture 10-4). The mixture 10-4 was kept at 25° C. for 20 hours (the resultant mixture is referred to as the mixture 10-5).

To 108.8 g of water (deionized water) was added 12.4 g of ethylene glycol and 12.6 g of gum arabic (Arabic Cole SS manufactured by SAN-EI YAKUHIN BOEKI CO., LTD.) to prepare an aqueous phase. All of the aqueous phase and all of the mixture 10-5 were mixed (the resultant mixture is referred to as the mixture 10-6).

The mixture 10-6 was stirred with a homogenizer (T.K. Autohomomixer, manufactured by PRIMIX CORP., revolution speed: 9,000 rpm) at room temperature to form liquid droplets in water (the resultant mixture is referred to as the mixture 10-7).

The mixture 10-7 was stirred at 60° C. for 24 hours to give an aqueous suspension composition of clothianidin microcapsules (hereinafter, referred to as the aqueous suspension composition 10).

The resultant microcapsules had a volume median diameter of 19.9 μm, wherein the net volume of the microcapsules with a particle diameter of 5 μm or less was 9.4% based on the gross volume of microcapsule particles, and the net volume of the microcapsules with a particle diameter of 50 μm or more was 0% based on the gross volume of microcapsule particles.

Production Example 11

250 g of clothianidin and 750 g of methyl O-acetylricinoleate (Ricsizer C-101, manufactured by Itoh Oil Chemicals Co., Ltd., content: 95.5%) were mixed (the resultant mixture is referred to as the mixture 11-1). The mixture 11-1 was stirred with a rotor-stator homogenizer (Polytron Homogenizer, manufactured by KINEMATICA AG) to grind clothianidin contained in the mixture 11-1 for about 10 minutes (the resultant mixture is referred to as the mixture 11-2). The clothianidin particles in the mixture 11-2 had a volume median diameter of 0.5 mm.

The mixture 11-2 was fed into Dyno Mill (manufactured by WILLY A. BACHOFEN AG. MASCHINENFABRIK, vessel size: 600 mL, filled with 1,150 g of spherical glass of 1 mm diameter, revolution speed of impeller: 12 m/sec as a peripheral speed) at a rate of 3 L/hr to further grind the clothianidin particles (the resultant mixture is referred to as the mixture 11-3). The clothianidin particles in the mixture 11-3 had a volume median diameter of 2.9 μm, wherein the net volume of the particles with a diameter of 10 μm or more was 3.3% based on the gross volume of microcapsule particles.

To 100 g of the mixture 11-3 was added 21.6 g of a polyisocyanate (Sumidur L-75, adduct of trimethylolpropane and toluenediisocyanate, manufactured by SUMIKA BAYER URETHANE CO., LTD.) at 25° C. (the resultant mixture is referred to as the mixture 11-4). The mixture 11-4 was kept at 25° C. for 20 hours (the resultant mixture is referred to as the mixture 11-5).

To 108.8 g of water (deionized water) were added 12.4 g of ethylene glycol and 12.6 g of gum arabic (Arabic Cole SS manufactured by SAN-EI YAKUHIN BOEKI CO., LTD.) to prepare an aqueous phase. All of the aqueous phase and all of the mixture 11-5 were mixed (the resultant mixture is referred to as the mixture 11-6).

The mixture 11-6 was stirred with a homogenizer (T.K. Autohomomixer, manufactured by PRIMIX CORP., revolution speed: 9,000 rpm) at room temperature to form liquid droplets in water (the resultant mixture is referred to as the mixture 11-7).

The mixture 11-7 was stirred at 60° C. for 24 hours to give an aqueous suspension composition of clothianidin microcapsules (hereinafter, referred to as the aqueous suspension composition 11).

The resultant microcapsules had a volume median diameter of 19.9 μm, wherein the net volume of the microcapsules with a particle diameter of 5 μm or less was 9.4% based on the gross volume of microcapsule particles, and the net volume of the microcapsules with a particle diameter of 50 μm or more was 0% based on the gross volume of microcapsule particles.

The aqueous suspension composition 11 was mixed with an aqueous solution prepared by mixing 68.05 g of water, 0.05 g of xanthan gum, 0.1 g of aluminum magnesium silicate, 0.5 g of disodium hydrogen phosphate and 0.1 g of Biohope L (preservative, manufactured by K.I. CHEMICAL INDUSTRY CO., LTD.) to give an aqueous suspension formulation of microcapsules. The aqueous suspension formulation had pH 7.9.

Production Example 12

250 g of clothianidin and 750 g of methyl O-acetylricinoleate (Ricsizer C-101, manufactured by Itoh Oil Chemicals Co., Ltd., content: 95.5%) were mixed (the resultant mixture is referred to as the mixture 12-1). The mixture 12-1 was stirred with a rotor-stator homogenizer (Polytron Homogenizer, manufactured by KINEMATICA AG) to grind clothianidin contained in the mixture 12-1 for about 10 minutes (the resultant mixture is referred to as the mixture 12-2). The clothianidin particles in the mixture 12-2 had a volume median diameter of 0.5 mm.

The mixture 12-2 was fed into Dyno Mill (manufactured by WILLY A. BACHOFEN AG. MASCHINENFABRIK, vessel size: 600 mL, filled with 1,150 g of spherical glass of 1 mm diameter, revolution speed of impeller: 12 m/sec as a peripheral speed) at a rate of 3 L/hr to further grind the clothianidin particles (the resultant mixture is referred to as the mixture 12-3). The clothianidin particles in the mixture 12-3 had a volume median diameter of 2.9 μm, wherein the net volume of the particles with a diameter of 10 μm or more was 3.3% based on the gross volume of microcapsule particles.

To 100 g of the mixture 12-3 was added 21.6 g of a polyisocyanate (Sumidur L-75, adduct of trimethylolpropane and toluenediisocyanate, manufactured by SUMIKA BAYER URETHANE CO., LTD.) at 25° C. (the resultant mixture is referred to as the mixture 12-4). The mixture 12-4 was kept at 25° C. for 20 hours (the resultant mixture is referred to as the mixture 12-5).

To 108.8 g of water (deionized water) were added 12.4 g of ethylene glycol and 12.6 g of gum arabic (Arabic Cole SS manufactured by SAN-EI YAKUHIN BOEKI CO., LTD.) to prepare an aqueous phase. All of the aqueous phase and all of the mixture 12-5 were mixed (the resultant mixture is referred to as the mixture 12-6).

The mixture 12-6 was stirred with a homogenizer (T.K. Autohomomixer, manufactured by PRIMIX CORP., revolution speed: 9,000 rpm) at room temperature to form liquid droplets in water (the resultant mixture is referred to as the mixture 12-7).

The mixture 12-7 was stirred at 60° C. for 24 hours to give an aqueous suspension composition of clothianidin microcapsules (hereinafter, referred to as the aqueous suspension composition 12).

The resultant microcapsules had a volume median diameter of 19.9 μm, wherein the net volume of the microcapsules with a particle diameter of 5 μm or less was 9.4% based on the gross volume of microcapsule particles, and the net volume of the microcapsules with a particle diameter of 50 μm or more was 0% based on the gross volume of microcapsule particles.

The aqueous suspension composition 12 was mixed with an aqueous solution prepared by mixing 68.55 g of water, 0.05 g of xanthan gum, 0.1 g of aluminum magnesium silicate, 0.1 g of sodium hydroxide and 0.1 g of Biohope L (preservative, manufactured by K.I. CHEMICAL INDUSTRY CO., LTD.) to give an aqueous suspension formulation of microcapsules. The aqueous suspension formulation had pH 7.9.

Production Example 13

250 g of clothianidin and 750 g of methyl O-acetylricinoleate (Ricsizer C-101, manufactured by Itoh Oil Chemicals Co., Ltd., content: 95.5%) were mixed (the resultant mixture is referred to as the mixture 13-1). The mixture 13-1 was stirred with a rotor-stator homogenizer (Polytron Homogenizer, manufactured by KINEMATICA AG) to grind clothianidin contained in the mixture 13-1 for about 10 minutes (the resultant mixture is referred to as the mixture 13-2). The clothianidin particles in the mixture 13-2 had a volume median diameter of 0.5 mm.

The mixture 13-2 was fed into Dyno Mill (manufactured by WILLY A. BACHOFEN AG. MASCHINENFABRIK, vessel size: 600 mL, filled with 1,150 g of spherical glass of 1 mm diameter, revolution speed of impeller: 12 m/sec as a peripheral speed) at a rate of 3 L/hr to further grind the clothianidin particles (the resultant mixture is referred to as the mixture 13-3). The clothianidin particles in the mixture 13-3 had a volume median diameter of 2.9 µm, wherein the net volume of the particles with a diameter of 10 µm or more was 3.3% based on the gross volume of microcapsule particles.

To 100 g of the mixture 13-3 was added 21.6 g of a polyisocyanate (Sumidur L-75, adduct of trimethylolpropane and toluenediisocyanate, manufactured by SUMIKA BAYER URETHANE CO., LTD.) at 25° C. (the resultant mixture is referred to as the mixture 13-4). The mixture 13-4 was kept at 25° C. for 20 hours (the resultant mixture is referred to as the mixture 13-5).

To 108.8 g of water (deionized water) were added 12.4 g of ethylene glycol and 12.6 g of gum arabic (Arabic Cole SS manufactured by SAN-EI YAKUHIN BOEKI CO., LTD.) to prepare an aqueous phase. All of the aqueous phase and all of the mixture 13-5 were mixed (the resultant mixture is referred to as the mixture 13-6).

The mixture 13-6 was stirred with a homogenizer (T.K. Autohomomixer, manufactured by PRIMIX CORP., revolution speed: 9,000 rpm) at room temperature to form liquid droplets in water (the resultant mixture is referred to as the mixture 13-7).

The mixture 13-7 was stirred at 60° C. for 24 hours to give an aqueous suspension composition of clothianidin microcapsules (hereinafter, referred to as the aqueous suspension composition 13).

The resultant microcapsules had a volume median diameter of 19.9 µm, wherein the net volume of the microcapsules with a particle diameter of 5 µm or less was 9.4% based on the gross volume of microcapsule particles, and the net volume of the microcapsules with a particle diameter of 50 µm or more was 0% based on the gross volume of microcapsule particles.

The aqueous suspension composition 13 was mixed with an aqueous solution prepared by mixing 68.05 g of water, 0.05 g of xanthan gum, 0.1 g of aluminum magnesium silicate, 0.5 g of dipotassium hydrogen phosphate and 0.1 g of Biohope L (preservative, manufactured by K.I. CHEMICAL INDUSTRY CO., LTD.) to give an aqueous suspension formulation of microcapsules. The aqueous suspension formulation had pH 7.2.

Production Example 14

250 g of clothianidin and 750 g of methyl O-acetylricinoleate (Ricsizer C-101, manufactured by Itoh Oil Chemicals Co., Ltd., content: 95.5%) were mixed (the resultant mixture is referred to as the mixture 14-1). The mixture 14-1 was stirred with a rotor-stator homogenizer (Polytron Homogenizer, manufactured by KINEMATICA AG) to grind clothianidin contained in the mixture 14-1 for about 10 minutes (the resultant mixture is referred to as the mixture 14-2). The clothianidin particles in the mixture 14-2 had a volume median diameter of 0.5 mm.

The mixture 14-2 was fed into Dyno Mill (manufactured by WILLY A. BACHOFEN AG. MASCHINENFABRIK, vessel size: 600 mL, filled with 1,150 g of spherical glass of 1 mm diameter, revolution speed of impeller: 12 m/sec as a peripheral speed) at a rate of 3 L/hr to further grind the clothianidin particles (the resultant mixture is referred to as the mixture 14-3). The clothianidin particles in the mixture 14-3 had a volume median diameter of 2.9 µm, wherein the net volume of the particles with a diameter of 10 µm or more was 3.3% based on the gross volume of microcapsule particles.

To 100 g of the mixture 14-3 was added 21.6 g of a polyisocyanate (Sumidur L-75, adduct of trimethylolpropane and toluenediisocyanate, manufactured by SUMIKA BAYER URETHANE CO., LTD.) at 25° C. (the resultant mixture is referred to as the mixture 14-4). The mixture 14-4 was kept at 25° C. for 20 hours (the resultant mixture is referred to as the mixture 14-5).

To 108.8 g of water (deionized water) were added 12.4 g of ethylene glycol and 12.6 g of gum arabic (Arabic Cole SS manufactured by SAN-EI YAKUHIN BOEKI CO., LTD.) to prepare an aqueous phase. All of the aqueous phase and all of the mixture 14-5 were mixed (the resultant mixture is referred to as the mixture 14-6).

The mixture 14-6 was stirred with a homogenizer (T.K. Autohomomixer, manufactured by PRIMIX CORP., revolution speed: 9,000 rpm) at room temperature to form liquid droplets in water (the resultant mixture is referred to as the mixture 14-7).

The mixture 14-7 was stirred at 60° C. for 24 hours to give an aqueous suspension composition of clothianidin microcapsules (hereinafter, referred to as the aqueous suspension composition 14).

The resultant microcapsules has a volume median diameter of 19.9 µm, wherein the net volume of the microcapsules with a particle diameter of 5 µm or less was 9.4% based on the gross volume of microcapsule particles, and the net volume of the microcapsules with a particle diameter of 50 µm or more was 0% based on the gross volume of microcapsule particles.

The aqueous suspension composition 14 was mixed with an aqueous solution prepared by mixing 68.25 g of water, 0.05 g of xanthan gum, 0.1 g of aluminum magnesium silicate, 0.3 g of disodium hydrogen phosphate and 0.1 g of Biohope L (preservative, manufactured by K.I. CHEMICAL INDUSTRY CO., LTD.) to give an aqueous suspension formulation of microcapsules. The aqueous suspension formulation had pH 6.2.

Production Example 15

250 g of clothianidin and 750 g of methyl O-acetylricinoleate (Ricsizer C-101, manufactured by Itoh Oil Chemicals Co., Ltd., content: 95.5%) were mixed (the resultant mixture is referred to as the mixture 15-1). The mixture 15-1 was stirred with a rotor-stator homogenizer (Polytron Homogenizer, manufactured by KINEMATICA AG) to grind clothianidin contained in the mixture 15-1 for about 10 minutes (the resultant mixture is referred to as the mixture 15-2). The clothianidin particles in the mixture 15-2 had a volume median diameter of 0.5 mm.

The mixture 15-2 was fed into Dyno Mill (manufactured by WILLY A. BACHOFEN AG. MASCHINENFABRIK, vessel size: 600 mL, filled with 1,150 g of spherical glass of 1 mm diameter, revolution speed of impeller: 12 m/sec as a peripheral speed) at a rate of 3 L/hr to further grind the clothianidin particles (the resultant mixture is referred to as the mixture 15-3). The clothianidin particles in the mixture 15-3 had a volume median diameter of 2.9 μm, wherein the net volume of the particles with a diameter of 10 μm or more wad 3.3% based on the gross volume of microcapsule particles.

To 100 g of the mixture 15-3 was added 21.6 g of a polyisocyanate (Sumidur L-75, adduct of trimethylolpropane and toluenediisocyanate, manufactured by SUMIKA BAYER URETHANE CO., LTD.) at 25° C. (the resultant mixture is referred to as the mixture 15-4). The mixture 15-4 was kept at 25° C. for 20 hours (the resultant mixture is referred to as the mixture 15-5).

To 108.8 g of water (deionized water) were added 12.4 g of ethylene glycol and 12.6 g of gum arabic (Arabic Cole SS manufactured by SAN-EI YAKUHIN BOEKI CO., LTD.) to prepare an aqueous phase. All of the aqueous phase and all of the mixture 15-5 were mixed (the resultant mixture is referred to as the mixture 15-6).

The mixture 15-6 was stirred with a homogenizer (T.K. Autohomomixer, manufactured by PRIMIX CORP., revolution speed: 9,000 rpm) at room temperature to form liquid droplets in water (the resultant mixture is referred to as the mixture 15-7).

The mixture 15-7 was stirred at 60° C. for 24 hours to give an aqueous suspension composition of clothianidin microcapsules (hereinafter, referred to as the aqueous suspension composition 15).

The resultant microcapsules had a volume median diameter of 19.9 μm, wherein the net volume of the microcapsules with a particle diameter of 5 μm or less was 9.4% based on the gross volume of microcapsule particles, and the net volume of the microcapsules with a particle diameter of 50 μm or more was 0% based on the gross volume of microcapsule particles.

The aqueous suspension composition 15 was mixed with an aqueous solution prepared by mixing 68.35 g of water, 0.05 g of xanthan gum, 0.1 g of aluminum magnesium silicate and 0.2 g of Proxel GXL (preservative, manufactured by Avecia K.K.) to give an aqueous suspension formulation of microcapsules. The aqueous suspension formulation had pH 7.4.

Comparative Production Example 1

An aqueous suspension composition (hereinafter, referred to as the comparative aqueous suspension composition 1) was produced in the same manner as in Production Example 1 except that the mixture 1-4 was kept at 20° C. for 1 hour.

Comparative Production Example 2

An aqueous suspension composition (hereinafter, referred to as the comparative aqueous suspension composition 2) was produced in the same manner as in Production Example 5 except that the mixture 5-4 was kept at 40° C. for 1 hour.

Comparative Production Example 3

An aqueous suspension composition (hereinafter, referred to as the comparative aqueous suspension composition 3) was produced in the same manner as in Production Example 1 except that the mixture 1-4 was kept at 50° C. for 1 hour.

Comparative Production Example 4

An aqueous suspension composition (hereinafter, referred to as the comparative aqueous suspension composition 4) was produced in the same manner as in Production Example 1 except that the mixture 1-4 was kept at 60° C. for 0.5 hour.

Test Example 1

A mixture of 0.5 g of each of the aqueous suspension compositions shown in the following Table 1 with 249.5 g of water was allowed to stand at room temperature for 2 hours. Then, the mixture was centrifuged at 3,000 rpm for 15 minutes. About 1 mL of the supernatant was separated, and 10 μL out of the 1 mL was subjected to high performance liquid chromatography to analyze the amount of clothianidin. Based on the analysis value thus obtained, the amount of clothianidin contained in the supernatant and the amount of clothianidin contained in a microcapsule were calculated. The residual rate of clothianidin contained in microcapsule based on the amount of clothianidin contained initially in the microcapsule is shown in Table 1.

TABLE 1

|  | Residual rate of clothianidin contained in microcapsule (%) |
| --- | --- |
| Aqueous suspension composition 1 | 79 |
| Aqueous suspension composition 2 | 78 |
| Aqueous suspension composition 3 | 79 |
| Aqueous suspension composition 4 | 91 |
| Aqueous suspension composition 5 | 82 |
| Aqueous suspension composition 6 | 76 |
| Comparative aqueous suspension composition 1 | 39 |
| Comparative aqueous suspension composition 2 | 41 |
| Comparative aqueous suspension composition 3 | 45 |
| Comparative aqueous suspension composition 4 | 38 |

Test Example 2

Each of the aqueous suspension compositions shown in the following Table 2 was diluted 200 times with water. Then, 0.4 mL of the dilution was spread over a glass petri dish of 6 cm diameter. Then, the dilution was air dried at room temperature. The petri dish was exposed to sunlight for 250 hours (cumulative illuminance: 1810 Lx).

To the petri dish was added 10 mL of acetonitrile and then stirred. Then, 10 μL of the mixture was subjected to high performance liquid chromatography to analyze the amount of clothianidin. Based on the analysis value thus obtained, the amount of clothianidin remaining in the petri dish was calculated. The residual rate of clothianidin based on the amount of clothianidin contained in the dilution initially spread over the petri dish is shown in Table 2.

TABLE 2

| | Residual rate of clothianidin (%) |
|---|---|
| Aqueous suspension composition 1 | 79 |
| Aqueous suspension composition 2 | 81 |
| Aqueous suspension composition 3 | 86 |
| Aqueous suspension composition 4 | 89 |
| Aqueous suspension composition 5 | 82 |
| Comparative aqueous suspension composition 1 | 54 |
| Comparative aqueous suspension composition 3 | 61 |

INDUSTRIAL APPLICABILITY

According to the method for producing a microcapsule of the present invention, it is possible to produce a microcapsule with the delayed release timing of a pesticidal compound contained therein as compared to a conventional microcapsule.

The invention claimed is:

1. A method for producing a microcapsule, which comprises the steps of:
    (1) first keeping an organic suspension phase mixture of a pesticidal compound, a compound represented by formula (I) and a polyisocyanate at 20 to 40° C. for 3 hours or more:

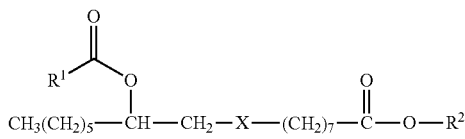

(I)

wherein X represents $CH_2$—$CH_2$— or $CH$=$CH$—, $R^1$ represents a C1-C4 alkyl group, and $R^2$ represents a C1-C4 alkyl group;
    (2) then adding the organic suspension phase mixture to an aqueous phase containing water and a polyol or a polyamine to obtain a second mixture, and mixing the second mixture to produce liquid droplets in water; and
    (3) then forming a film of polyurethane or polyurea around the droplets,
    wherein the weight ratio of the pesticidal compound to the compound represented by formula (I) is from 10:100 to 100:100;
    wherein the weight ratio of water is in a range from 0.8 to 2 times the weight of the mixture obtained in the step (1).

2. The method according to claim 1, wherein the compound represented by formula (I) is a C1-C4 alkyl ester of O-acetylricinoleic acid.

3. The method according to claim 1, wherein the compound represented by formula (I) is methyl O-acetylricinoleate.

4. The method according to claim 1, wherein the pesticidal compound is a solid pesticidal compound.

5. The method according to claim 1, wherein the pesticidal compound is a neonicotinoid compound.

6. The method according to claim 1, wherein the pesticidal compound is clothianidin.

7. A microcapsule produced by the method according to claim 1.

8. The method according to claim 1, wherein the first keeping period is 5 hours or more.

9. The method according to claim 1, wherein the first keeping period is 10 hours or more.

* * * * *